(12) United States Patent
Akita et al.

(10) Patent No.: US 9,934,944 B2
(45) Date of Patent: Apr. 3, 2018

(54) PLASMA INDUCED FLOW ELECTRODE STRUCTURE, PLASMA INDUCED FLOW GENERATION DEVICE, AND METHOD OF MANUFACTURING PLASMA INDUCED FLOW ELECTRODE STRUCTURE

(71) Applicant: KABUSHIKI KAISHA TOSHIBA, Tokyo (JP)

(72) Inventors: Masato Akita, Kanagawa (JP); Akio Ui, Tokyo (JP); Yasushi Sanada, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 75 days.

(21) Appl. No.: 15/210,115

(22) Filed: Jul. 14, 2016

(65) Prior Publication Data
US 2017/0018409 A1 Jan. 19, 2017

(30) Foreign Application Priority Data

Jul. 15, 2015 (JP) .................................. 2015-141202

(51) Int. Cl.
*H01J 37/32* (2006.01)
*H01J 9/18* (2006.01)
(Continued)

(52) U.S. Cl.
CPC .......... *H01J 37/32541* (2013.01); *A61L 9/22* (2013.01); *H01J 9/18* (2013.01); *H01J 37/32348* (2013.01);
(Continued)

(58) Field of Classification Search
None
See application file for complete search history.

(56) References Cited

U.S. PATENT DOCUMENTS 5,981,899 A * 11/1999 Perrin ............... H01J 37/32091
118/723 R
RE39,020 E * 3/2006 Hama ................. C23C 16/4404
118/715
(Continued)

FOREIGN PATENT DOCUMENTS

JP  2005-515843  6/2005
JP  2005-342708  12/2005
(Continued)

OTHER PUBLICATIONS

Corke, T.C., et al., "Dielectric Barrier Discharge Plasma Actuators for Flow Control", Annu. Rev. Fluid Mech., vol. 42, pp. 505-529 (2010).
(Continued)

*Primary Examiner* — Douglas W Owens
*Assistant Examiner* — Srinivas Sathiraju
(74) *Attorney, Agent, or Firm* — Finnegan, Henderson, Farabow, Garrett & Dunner, L.L.P.

(57) ABSTRACT

In one embodiment, a plasma induced flow electrode structure has an electrode block, an insulating layer and an electrode layer. The electrode block has first and second surfaces and through holes penetrating between these first and second surfaces. The insulating layer is disposed on the first surface and inside the through holes. The electrode layer is disposed on the insulating layer of the first surface.

15 Claims, 13 Drawing Sheets

(51) Int. Cl.
  *A61L 9/22* (2006.01)
  *H05H 1/24* (2006.01)
(52) U.S. Cl.
  CPC ..... *H01J 37/32844* (2013.01); *H05H 1/2406* (2013.01); *H05H 2001/2412* (2013.01); *H05H 2001/2418* (2013.01); *H05H 2001/2437* (2013.01); *Y02C 20/30* (2013.01)

(56) References Cited

U.S. PATENT DOCUMENTS

| | | | |
|---|---|---|---|
| 7,196,283 B2* | 3/2007 | Buchberger, Jr. | H01J 37/32082 156/345.34 |
| 7,225,754 B2* | 6/2007 | Nakano | C23C 16/5096 118/723 E |
| 7,507,934 B2 | 3/2009 | Kondou et al. | |
| 7,543,546 B2* | 6/2009 | Shibata | H01J 37/32009 118/723 E |
| 7,547,861 B2* | 6/2009 | Jorgensen | H05H 1/34 164/46 |
| 7,721,673 B2* | 5/2010 | Du | H01J 37/32009 118/723 E |
| 8,070,911 B2* | 12/2011 | Himori | H01J 37/32082 118/723 E |
| 8,128,831 B2* | 3/2012 | Sato | H01L 21/0273 216/41 |
| 8,367,966 B2* | 2/2013 | Takahashi | H05H 1/2406 118/723 R |
| 8,545,671 B2* | 10/2013 | Honda | H01J 37/32091 118/723 E |
| 8,636,871 B2* | 1/2014 | Sawada | H01J 37/32091 118/723 E |
| 8,773,018 B2* | 7/2014 | Hensley | H05B 41/2806 315/111.01 |
| 9,105,705 B2* | 8/2015 | Pays-Volard | H01L 21/68771 |
| 9,117,636 B2* | 8/2015 | Koo, II | H01J 37/32348 |
| 9,220,162 B2* | 12/2015 | Takenoshita | H05H 1/2406 |
| 9,468,698 B2* | 10/2016 | Ui | A61L 9/16 |
| 9,660,182 B2* | 5/2017 | Sone | H01L 43/12 |
| 9,757,487 B2* | 9/2017 | Roy | A61L 2/14 |
| 2005/0249646 A1 | 11/2005 | Iwama et al. | |
| 2006/0152163 A1* | 7/2006 | Miki | F01N 3/0892 315/111.21 |
| 2008/0063577 A1 | 3/2008 | Crowe et al. | |
| 2008/0131333 A1* | 6/2008 | Tzeng | B01D 53/32 422/168 |
| 2010/0033096 A1* | 2/2010 | Choi | H01J 37/32091 315/111.21 |
| 2012/0228263 A1* | 9/2012 | Ui | H01J 37/32091 216/71 |
| 2012/0315194 A9 | 12/2012 | Rousseau et al. | |
| 2013/0061870 A1* | 3/2013 | Ui | B08B 7/00 134/1.1 |
| 2013/0064710 A1 | 3/2013 | Jacob | |
| 2014/0110059 A1* | 4/2014 | Huang | H01J 37/32091 156/345.27 |
| 2015/0104896 A1* | 4/2015 | Dybek | C23C 8/36 438/57 |
| 2015/0123541 A1* | 5/2015 | Baek | C23C 16/503 315/111.21 |
| 2015/0137677 A1* | 5/2015 | Sohn | H01T 19/04 313/268 |
| 2015/0265740 A1* | 9/2015 | Ui | A61L 9/16 422/121 |
| 2016/0027619 A1* | 1/2016 | Sato | C23C 16/50 216/67 |
| 2016/0064260 A1* | 3/2016 | Berry, III | H01L 21/67069 438/712 |
| 2016/0071698 A1* | 3/2016 | Okino | D06M 10/02 252/500 |
| 2016/0262251 A1* | 9/2016 | Jung | H05H 1/24 |
| 2017/0007958 A1* | 1/2017 | Ui | B01D 53/32 |

FOREIGN PATENT DOCUMENTS

| | | |
|---|---|---|
| JP | 2006-302918 | 11/2006 |
| JP | 2007-80772 | 3/2007 |
| JP | 2007-258090 | 10/2007 |
| JP | 2008-289801 | 12/2008 |
| JP | 2010-532253 | 10/2010 |
| JP | 2015-162004 | 10/2015 |

OTHER PUBLICATIONS

Okochi, S. et al. (2010). "Characteristics of Micro Plasma Actuator," *The University of Tokyo, Department of Mechanical Engineering*, vol. 29; pp. 271-276.

* cited by examiner

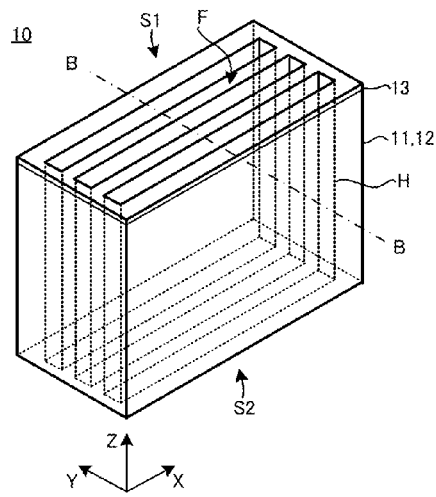
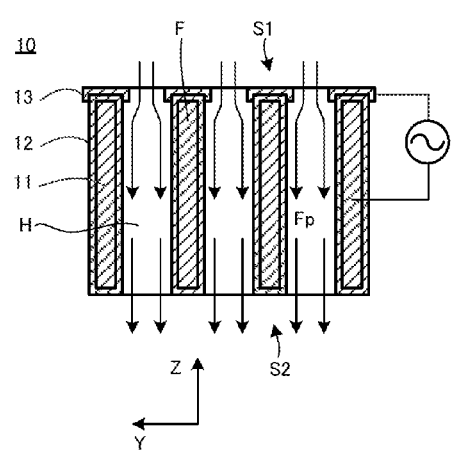
FIG. 1A  FIG. 1B
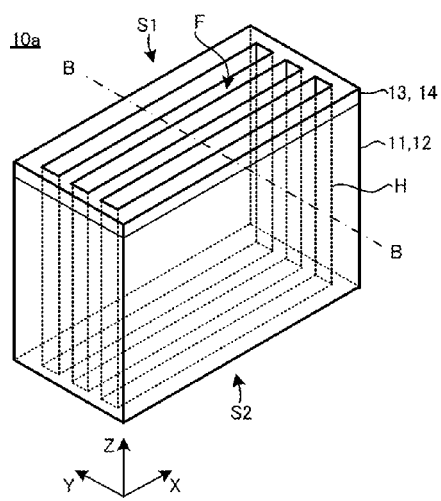
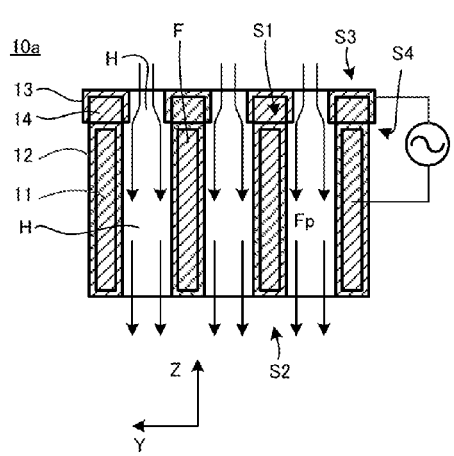
FIG. 2A  FIG. 2B

PLASMA INDUCED FLOW ELECTRODE STRUCTURE, PLASMA INDUCED FLOW GENERATION DEVICE, AND METHOD OF MANUFACTURING PLASMA INDUCED FLOW ELECTRODE STRUCTURE

CROSS REFERENCE TO RELATED APPLICATION

This application is based upon and claims the benefit of priority from Japanese Patent Application No. 2015-141202, filed on Jul. 15, 2015; the entire contents of which are incorporated herein by reference.

FIELD

Embodiments described herein relate generally to a plasma induced flow electrode structure, a plasma induced flow generation device, and a method of manufacturing the plasma induced flow electrode structure.

BACKGROUND

A plasma induced flow is a gas flow generated by application of high voltage of high frequency between electrodes separated by a dielectric. As a result that discharge is carried out in a state where one of the two electrodes is not insulated from outside air and the other is insulated from outside air, a gas flow (plasma induced flow) from the former to the latter occurs.

The plasma induced flow has a smaller flow amount per input power and a lower efficiency compared with a gas flow from a general air blower such as a fan and a blower, but the plasma induced flow can be made to flow only in a neighborhood of a surface of the electrode. Thus, by providing a plasma induced flow generation device in a wing of an aircraft or a blade of wind power generation to prevent a rear turbulent flow clue to flow peeling, it is possible to suppress reduction of lift and increase in an air resistance.

Meanwhile, attention is paid to plasma itself in the plasma induced flow as a new means of air purification replacing a catalyst and an adsorbent, and discharge methods by various electrode configurations such as point discharge and mesh discharge are devised. As active species occurring in discharge in the atmosphere, there can be cited negative ion and the like such as ozone, OH radical and $O_2^-$. Among the above, OH radical has a large air purification ability but also has a short life because of being active. Thus, a method is devised in which OH radical is made to be contained in a cluster of water and used for air purification.

Here, a density of the active species is preferable to be high in terms of an efficiency of processing. Meanwhile, in view of human health, it is necessary to limit the density of the active species in air. Thus, in order to achieve both efficiency of processing and human health, it is conceived to take in air to be purified by a fan or a blower and to carry out purification in a local space in which the density of the active species is high.

As a discharge structure for active species generation, a point discharge structure or a mesh discharge structure is adopted. However, it is difficult to mention these discharge structures as being able to efficiently use OH radical which only has a diffusion operating life of about several mm from a discharge point. Therefore, there is devised a device in which electrode fins that generate plasma induced flows are stacked (plasma induced flow electrode stack (hereinafter, abbreviated as "PA stack")) and air is taken in by the plasma induced flows, to improve a processing efficiency.

Though the PA stack can be formed by stacking electrodes, its shape is limited. For the purpose of air purification, an electrode configuration in which parallel slits (spaces between electrodes) are disposed in multiple stages is not necessarily optimum. It is sometimes desirable that an outer shape of the electrode configuration is circular and that the slits are concentric. However, it is not easy to make a proper structure by stacking electrodes.

BRIEF DESCRIPTION OF THE DRAWINGS

FIG. 1A is a perspective view of a plasma induced flow electrode structure 10 according to a first embodiment;

FIG. 1B is a cross-sectional view of the plasma induced flow electrode structure 10 according to the first embodiment;

FIG. 2A is a perspective view of a plasma induced flow electrode structure 10a according to a second embodiment;

FIG. 2B is a cross-sectional view of the plasma induced flow electrode structure 10a according to the second embodiment;

DETAILED DESCRIPTION

Figure 3:
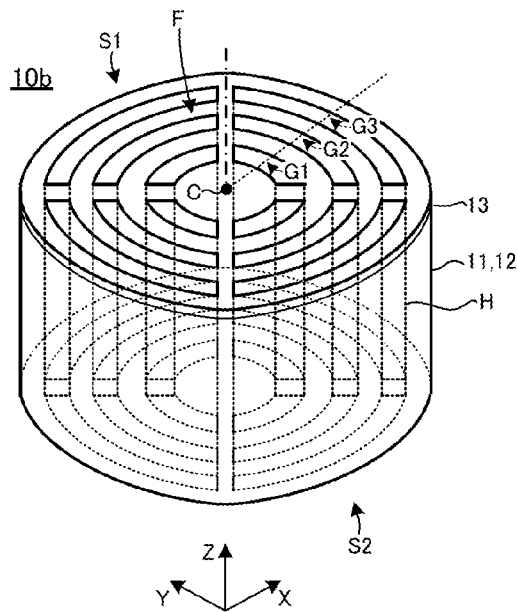
FIG. 3 is a perspective view of a plasma induced flow electrode structure 10b according to a modification example 1.

In one embodiment, a plasma induced flow electrode structure has an electrode block, an insulating layer and an electrode layer. The electrode block has first and second surfaces and a plurality of through holes penetrating between these first and second surfaces. The insulating layer is disposed on the first surface and inside the plurality of through holes. The electrode layer is disposed on the insulating layer of the first surface.

Hereinafter, embodiments will be described in detail with reference to the drawings.

A. Plasma Induced Flow Electrode Structure

Plasma induced flow electrode structures according to embodiments will be described.

First Embodiment

FIG. 1A is a perspective view of a plasma induced flow electrode structure 10 according to a first embodiment. FIG. 1B is a cross-sectional view illustrating a state where the plasma induced flow electrode structure 10 is cut along a line B-B.

The plasma induced flow electrode structure 10 has an electrode block 11, an insulating layer 12 and an electrode layer 13.

The electrode block 11 is constituted with a block of a conductor, and functions as an electrode member (ground electrode or anode electrode) for plasma generation. As the conductor, a metal material such as aluminium, brass, copper and stainless steel can be used.

Here, the electrode block 11 has an outer shape of an almost rectangular parallelepiped, but can have various shapes such as an almost columnar shape, as will be described later.

The electrode block 11 has surfaces S1, S2 and a plurality of through holes H. The surfaces S1, S2 are two main surfaces on opposite sides to each other of the rectangular parallelepiped shape. The through hole H penetrates between the surfaces S1, S2. Here, the through hole H has an almost rectangular parallelepiped shape, but can have various shapes such as an almost column shape, as will be described later.

An electrode fin F of an almost rectangular parallelepiped shape (almost plate shape) is disposed between the through holes H.

The insulating layer 12 is a layer to retain insulation between the electrode block 11 and the electrode layer 13 and to prevent direct discharge between the electrode block 11 and the electrode layer 13. The insulating layer 12 covers the entire of the electrode block 11 which includes the surfaces S1, S2 and the plurality of through holes H.

Here, it is also possible to dispose the insulating layer 12 in a limited way. For example, it is possible that the insulating layer 12 is not disposed on the surface S2. Further, the insulating layer 12 may be disposed only on the electrode 13 and in its neighborhood. However, in order to prevent the direct discharge between the electrode block 11 and the electrode layer 13, it is preferable that the insulating layer 12 with a width of a certain degree is disposed between the electrode layer 13 and the exposed electrode block 11 (where the insulating layer 12 is not disposed).

The electrode layer 13 is a conductive coating film made of a conductor such as copper, and functions as a cathode electrode for plasma generation. The electrode layer 13 is disposed on the surface S1 and on the insulating layer 12 in a neighborhood thereof. In other words, the electrode layer 13 is disposed on the insulating layer 12 of the surface S1 and extends onto the insulating layer 12 inside the plurality of insulating holes H.

It is also possible to dispose the electrode layer 13 in a periphery of an opening of the through hole H and not to dispose inside the through hole H. However, in order to generate a plasma induced flow Fp effectively, it is preferable to dispose the electrode layer 13 not only in the periphery of the opening of the through hole H but also inside the through hole H in a neighborhood of that opening.

Here, it is possible that the electrode layer 13 is not disposed in the peripheries of the openings of a part of the through holes H nor inside the through holes H. In this way, the plasma induced flow Fp can be made not to be generated in a part of the through holes H. Details thereof will be explained in later-described modification examples 4, 5.

As illustrated in FIG. 1B, when AC high voltage is applied to between the electrode block 11 (electrode fin F) and the electrode layer 13 by a power supply, a plasma induced flow Fp which flows from the surface S1 (electrode layer 13) toward the surface S2 inside the through hole H is generated. By application of the AC high voltage, air is ionized in the neighborhood of the electrode layer 13 and plasma is generated. As a result that this plasma proceeds toward a direction of the electrode fin F inside the through hole H, the plasma becomes the plasma induced flow Fp. As is already described, air can be purified by active species such as OH radical contained in the plasma in the plasma induced flow.

Second Embodiment

FIG. 2A is a perspective view of a plasma induced flow electrode structure 10a according to a second embodiment. FIG. 2B is a cross-sectional view illustrating a state where the plasma induced flow electrode structure 10a is cut along a ling B-B.

The plasma induced flow electrode structure 10a has an electrode block 11, an insulating layer 12, an electrode layer 13 and an insulating member 14.

The insulating member 14 (insulating plate), by preventing approach between the electrode block 11 and the electrode layer 13, carries out insulation and prevents direct discharge more securely, and intends reduction of an electrostatic capacitance.

The insulating member 14 is constituted with an insulating material and has an outer shape of an almost flat plate shape. The insulating member 14 has surfaces S3, S4 (third and fourth surfaces) on opposite sides to each other and a second through hole H penetrating between these surfaces S3. S4 and corresponding to a through hole H of the electrode block 11. The insulating member 14 has almost the same cross-sectional shape as that of the electrode block 11. In other words, the surfaces S3, S4 of the insulating member 14 have a shape (here, planar rectangle) and a size corresponding to a surface S1 of the electrode block 11. The through hole H of the insulating member 14 has a shape (here, planar rectangle) and a size corresponding to the through hole H of the electrode block 11.

In the present embodiment, the electrode layer 13 is disposed on the insulating member 14, not on the insulating layer 12. In other words, the insulating member 14 is disposed between the insulating layer 12 and the electrode layer 13. Further, the electrode layer 13 becomes a conductive coating film made of a conductor such as copper which covers the insulating member 14.

The electrode layer 13 is disposed on the surface S3 and on the insulating member 14 in a neighborhood thereof. In other words, the electrode layer 13 is disposed on the surface S3 and extends to the inside of the through hole H of the insulating member 14.

It is also possible to dispose the electrode layer 13 in a periphery of the opening of the through hole H of the insulating member 14 and not to dispose inside the through hole H. However, in order to generate a plasma induced flow Fp effectively, it is preferable to dispose the electrode layer 13 not only in the periphery of the opening of the through hole H of the insulating member 14 but also inside the through hole H in a neighborhood of that opening.

Here, it is possible that the electrode layer 13 is not disposed in the peripheries of the openings of a part of the through hole H of the insulating member 14 nor inside the through holes H. In this way, the plasma induced flow Fp can be made not to be generated in a part of the through holes H.

The electrode layer 13 is not disposed on the surface S4 (between the insulating member 14 and the electrode block 11 (electrode fin F) of the insulating member 14. This is for preventing approach of the electrode layer 13 and the electrode block 11 (electrode fin F).

Since the electrode block 11 and the insulating layer 12 of the present embodiment are not largely different from those in the first embodiment, explanation thereof will be omitted.

In the plasma induced flow electrode structure 10a also, a plasma induced flow Fp is generated by application of AC high voltage to between the electrode block 11 (electrode fin F) and the electrode layer 13.

Modification Examples 1 to 5

FIG. 3 is a perspective view of a plasma induced flow electrode structure 10b according to a modification example 1.

The plasma induced flow electrode structure 10b, in which an outer shape of an electrode block 11 is an almost columnar shape, is a through hole H of an almost partial cylinder shape. A coaxial shape as above is suitable to be used by being disposed inside a circular piping or being connected to a circular piping.

Here, the electrode block 11 is almost column-shaped and has a center line C as a center of symmetry, and a shape of the through hole H is an almost arc shape with a width G. On this occasion, the widths (spaces between electrode fins F) G (G1 to G3) of the through holes H may be differentiated in correspondence with positions of the through holes H. For example, as a distance from the center line C of the electrode block 11 becomes larger, the width G is made larger (G1<G2<G3).

In the circular piping, the farther it goes from a center thereof (the nearer it goes to an inner wall of the piping), a flow velocity of gas flowing inside the piping becomes smaller. Therefore, by changing a size of the width G in correspondence with the distance from the center line C of the electrode block 11, it is possible to reduce varieties of processing amounts of gas in the respective through holes H in the plasma induced flow electrode structure 10b.

As described above, here, the electrode block 11 is almost column-shaped and has the center line C as the center of symmetry, and the shape of the through hole H is the almost arc shape with the width G. In more general cases (for example, cases including later-described FIG. 4 and FIG. 5) also, changing the size (for example, width G, diameter) of the through hole H in correspondence with the distance from the center of the electrode block 11 (electrode member) is effective in reducing varieties of the processing amounts of gas.

In a case of the circular piping (electrode block 11 is almost column-shaped), generally, it is considered that as a distance from a center becomes larger a width G should be made larger. However, a flow velocity distribution of gas passing through the through hole H may change depending on a shape of the through hole H. Thus, there may be a case where the width G should be made smaller as the distance becomes large.

Figure 4:
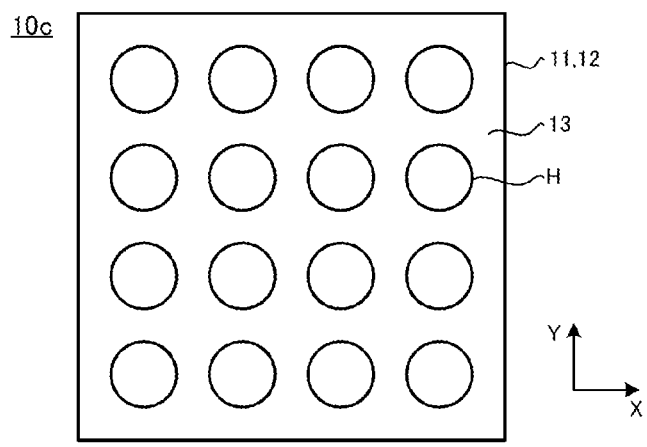
FIG. 4 is an upper surface view of a plasma induced flow electrode structure 10c according to a modification example 2.

FIG. 4 is an upper surface view of a plasma induced flow electrode structure 10c according to a modification example 2.

In the plasma induced flow electrode structure 10c, an outer shape of an electrode block 11 is an almost rectangular parallelepiped shape and comparatively small through holes H of an almost column shape are arranged. By using a porous shape in which small through holes are arranged as above, an air supply amount of the plasma induced flow electrode structure 10c can be increased.

Figure 5:
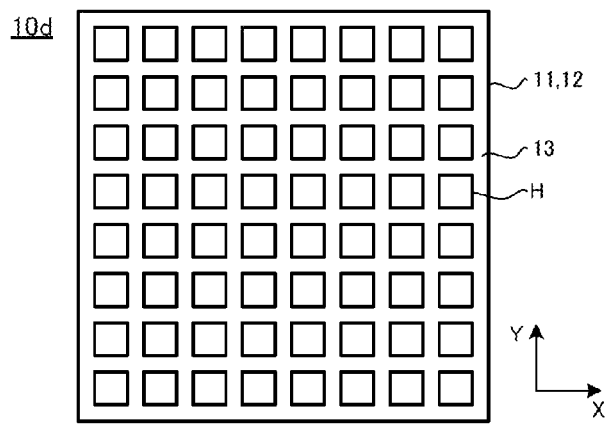
FIG. 5 is an upper surface view of a plasma induced flow electrode structure 10d according to a modification example 3.

FIG. 5 is an upper surface view of a plasma induced flow electrode structure 10d according to a modification example 3.

In the plasma induced flow electrode structure 10d, an outer shape of an electrode block 11 is an almost rectangular parallelepiped shape and comparatively small through holes H of an almost rectangular parallelepiped shape are arranged. By using a shape of lattice or honeycomb as above, an air supply amount of the plasma induced flow electrode structure 10d can be increased.

Figure 6A:
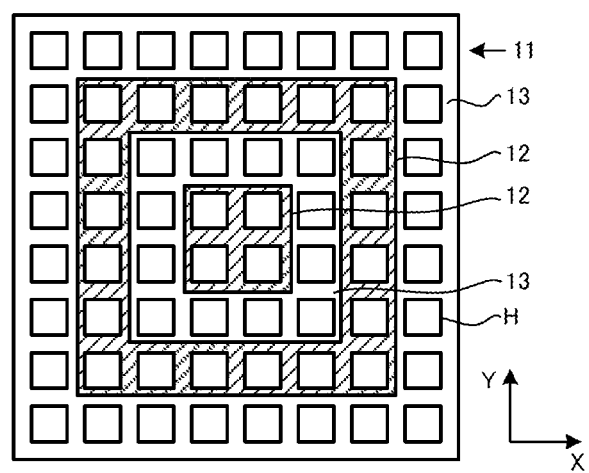
FIG. 6A is an upper surface view of a plasma induced flow electrode structure 10e according to a modification example 4.
Figure 6B:
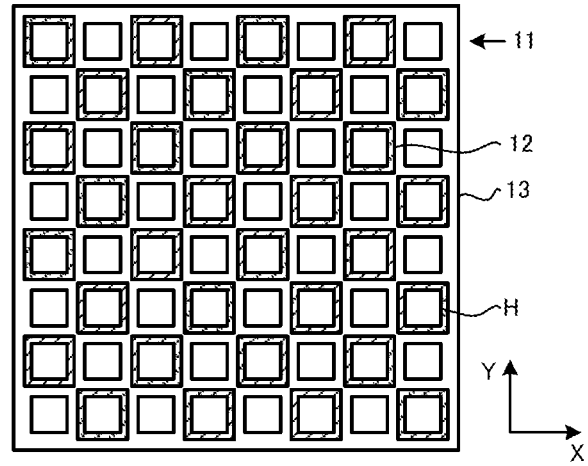
FIG. 6B is an upper surface view of a plasma induced flow electrode structure 10f according to the modification example 4.

FIG. 6A and FIG. 6B are upper surface views of plasma induced flow electrode structures 10e, 10f according to a modification example 4.

In each of the plasma induced flow electrode structures 10e, 10f an electrode layer 13 is disposed only in a part of openings of through holes H disposed on a surface S1 of an electrode block 11, and an insulating layer 12 is exposed in the other part. Here, hatching is given to the exposed insulating layer 12, for the sake of comprehensiveness.

From the above, a plasma induced flow Fp can be generated only in a part of the plurality of through holes H.

Here, an electrode layer 13 may be disposed on a surface S2 side of the through hole H where the electrode layer 13 is not disposed on a surface S1 side. In other words, the electrode layer 13 (second electrode layer) is disposed in peripheries of a part of the plurality of through holes H (where the electrode layer 13 is not disposed on the surface S1 side) on the surface S2 (second surface).

From the above, it is possible to generate a plasma induced flow Fp of a direction from the surface S2 toward the surface S1 in that through hole H. It means that the plasma induced flow Fp is generated in a direction (forward direction) from the surface S1 toward the surface S2 or in a direction (reverse direction) from the surface S2 toward the surface S1, depending on the through hole. In other words, it is possible to distribute the plasma induced flows Fp in the forward direction and the reverse direction accordingly.

Figure 7A:
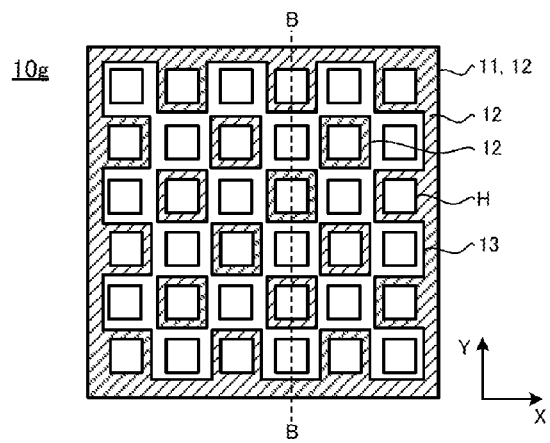
FIG. 7A is an upper surface view of a plasma induced flow electrode structure 10g according to a modification example 5.
Figure 7B:
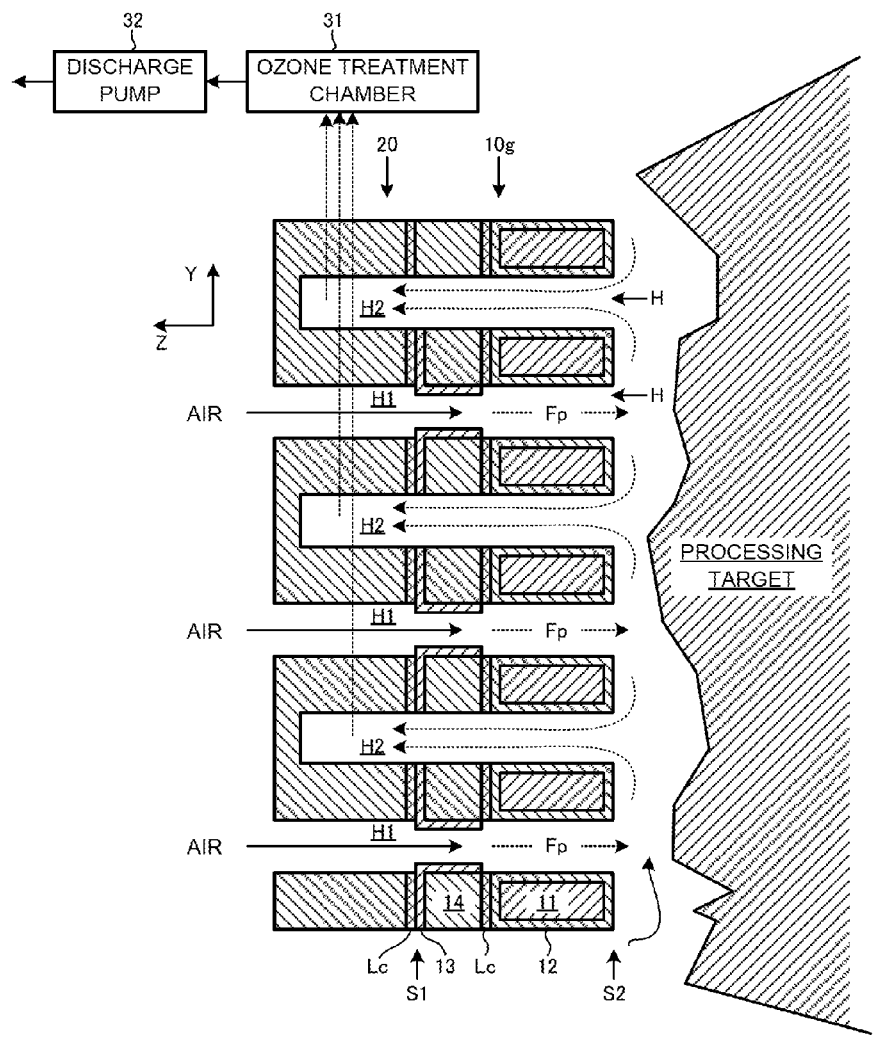
FIG. 7B is a cross-sectional view of the plasma induced flow electrode structure 10g according to the modification example 5.

FIG. 7A and FIG. 7B are an upper surface view and a cross-sectional view of a plasma induced flow electrode structure 10g according to a modification example 5. FIG.

7B is the cross-sectional view illustrating a state where the plasma induced flow electrode structure 10g is cut along a line B-B.

Here, the plasma induced flow electrode structure 10g is connected to a collection manifold 20.

In the plasma induced flow electrode structure 10g, a through hole H where an electrode layer 13 is disposed and a through hole H where the electrode layer 13 is not disposed are alternately disposed. Here, in FIG. 7B, hatching is given to an exposed insulating layer 12 for the sake of comprehensiveness.

The collection manifold 20 has hole portions H1, H2 corresponding to through holes H. The hole portion H1 is a through hole and is communicated with the through hole H where the electrode layer 13 is disposed. The hole portion H2 is a non-through hole and is communicated with the through hole H where the electrode layer 13 is not disposed and connected to an ozone treatment chamber 31 and an exhaust pump 32.

In the ozone treatment chamber 31, an ozone catalyst which decomposes ozone is disposed.

The exhaust pump 32 sucks in gas in the hole portion H2 via the ozone treatment chamber 31 and discharges to the outside.

When voltage is applied to the plasma induced flow electrode structure 10g to drive the exhaust pump 32, operation described below is carried out.

By voltage application to the plasma induced flow electrode structure 10g, a plasma induced flow Fp is generated and air is sucked in from the hole portion H1. The air having been sucked in is ionized and becomes a plasma induced flow Fp, and is sprayed to a processing target. The sprayed plasma induced flow Fp is made to go through the hole portion H2 by the exhaust pump 32, ozone being removed in the ozone treatment chamber 31, and then is exhausted to the outside.

Since ozone is generated not a little in plasma discharge under the atmosphere, generally, isolation of ozone is required in a device for a surface treatment or sterilization using discharge, in order not to give an influence to a human body. However, in the plasma induced flow electrode structure 10, it is possible to spray ozone or oxygen active species evenly by the entire surface (surface S1) of a duct. Further, as a result that a part of the through holes H is made not for spraying but for sucking in, ozone or oxygen active species can be made not to be diffused improperly under the atmosphere.

B. Method of Manufacturing Plasma Induced Flow Electrode Structure

A method of manufacturing the plasma induced flow electrode structure according to the embodiment will be described.

Third Embodiment

A method of manufacturing a plasma induced flow electrode structure according to a third embodiment will be described. In the present embodiment, the plasma induced flow electrode structure 10 according to the first embodiment can be manufactured.

Figure 8:
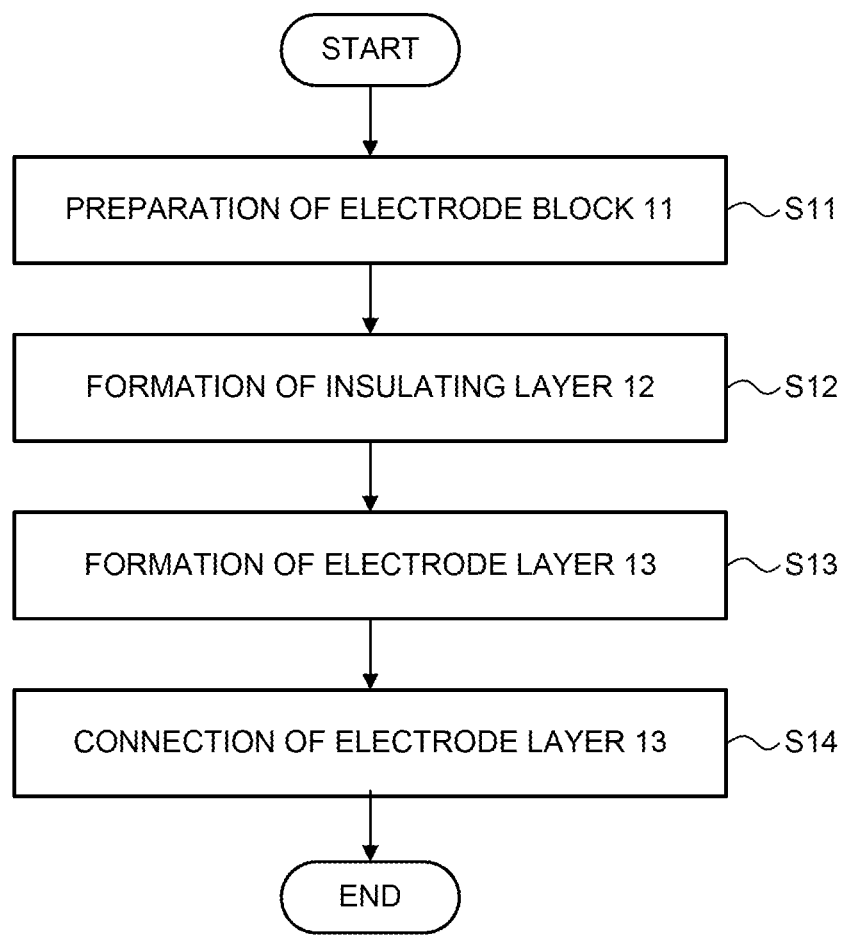
FIG. 8 is a flowchart illustrating a manufacturing procedure of a plasma induced flow electrode structure according to a third embodiment.

FIG. 8 is a flowchart illustrating a manufacturing procedure of the plasma induced flow electrode structure according to the third embodiment. FIG. 9 to FIG. 12 are front views and cross-sectional views illustrating the plasma induced flow electrode structure 10 in being manufactured in the present embodiment. FIG. 9(b) to FIG. 11(b) are cross-sectional views illustrating states where the plasma induced flow electrode structures 10 of FIG. 9(a) to FIG. 11(a) are cut along lines B-B, respectively.

Figure 9:
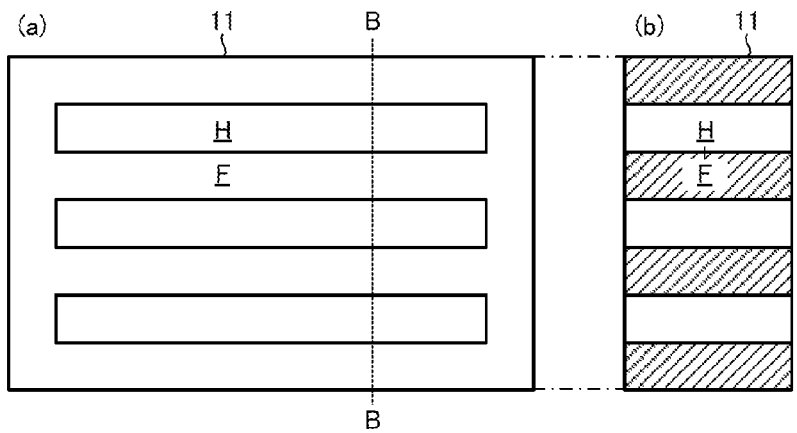
FIG. 9 are a front view and a cross-sectional view illustrating the plasma induced flow electrode structure 10 in being manufactured.

(1) Preparation of Electrode Block 11 (Step S11, FIG. 9)

An electrode 11 is fabricated by integral cutting from an electrode block (for example, copper block). Consequently, the electrode block 11 which has an electrode fin F to be a ground electrode (or anode electrode) is fabricated.

Figure 10:
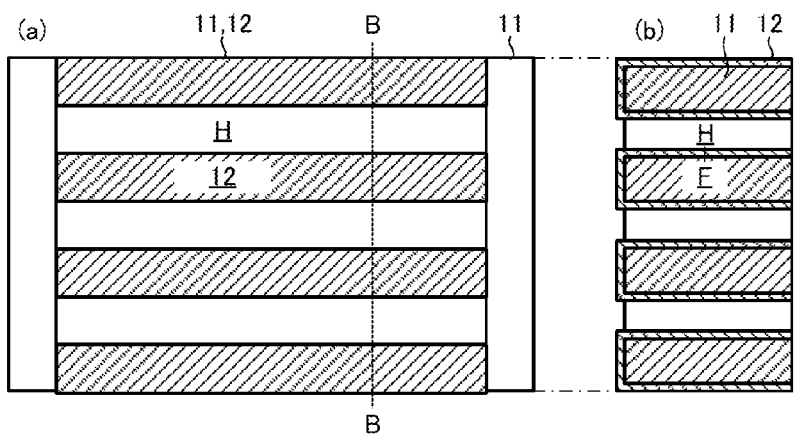
FIG. 10 to FIG. 11 are front views and cross-sectional views illustrating the plasma induced flow electrode structure 10 in being manufactured.

(2) Formation of Insulating Layer 12 (Step S12, FIG. 10)

An insulating layer 12 is formed on the electrode fin F of the electrode block 11 in a manner to go around to a surface S1 side (air flow-in side). As the insulating layer 12, a polyimide film (insulating film) of about 100 ppm in thickness is used, and this film is bonded to the electrode block 11. At a time of bonding, attention is paid so as not to leave an air bubble between the electrode fin F and the insulating layer 12 (polyimide film).

Figure 11:
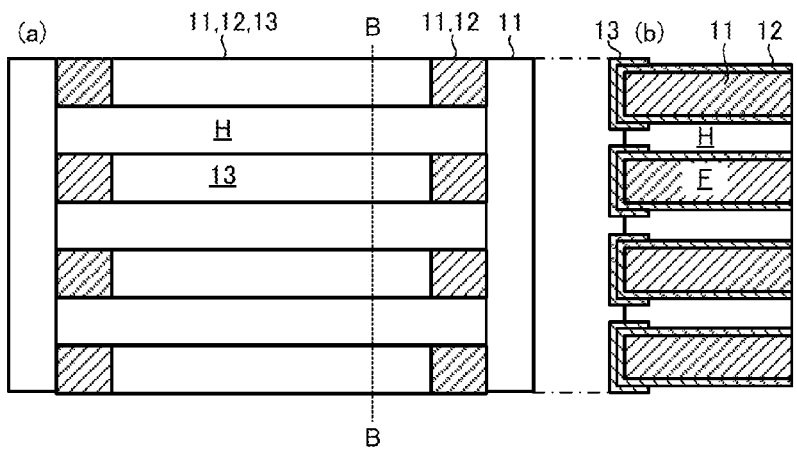

(3) Formation of Electrode Layer 13 (Step S13, FIG. 11)

Next, an electrode layer 13 is formed in an inner side by about 5 mm from a region which is not covered by the insulating layer 12 (polyimide film) of the electrode fin F.

A copper foil is used as the electrode layer 13 and the copper foil is bonded to the insulating layer 12 (polyimide film). When the insulating layer 12 cannot maintain a distance between the exposed electrode fin F and the electrode layer 13, there is a possibility that a short circuit occurs between the electrode fin F and the electrode layer 13 and that a plasma induced flow cannot be maintained.

Further, the electrode layer 13 is formed both on the surface S1 of the electrode block 11 and in a region inside a through hole H by about 1 mm from the surface S1. With regard to the electrode 13 (copper foil), attention is paid to remove an air bubble similarly to in a case of the insulating layer 12 (polyimide film).

However, since discharge to become a drive force of a plasma induced flow occurs only in an end surface (surface S1) of the electrode layer 13, it is not necessary to make the electrode layer 13 go around into the through hole H much, and it suffices that the end surface (surface S1) of the electrode layer 13 is pointed in an axis direction of the through hole H.

Figure 12:
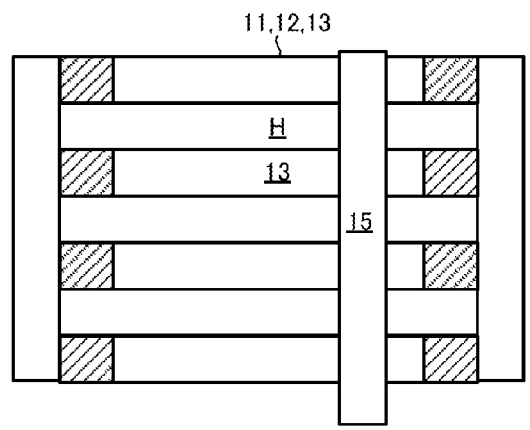
FIG. 12 is a front view illustrating the plasma induced flow electrode structure 10 in being manufactured.

(4) Connection of Electrode 13 (Step S14, FIG. 12)

In the present embodiment, since the electrode layer 13 is divided into four and not electrically conducted, a conduction portion 15 (copper foil) is added and the four electrode layers 13 corresponding to respective through holes H are electrically connected.

COMPARATIVE EXAMPLE

A plasma induced flow electrode structure according to a comparative example and its manufacturing method will be described.

Figure 13:
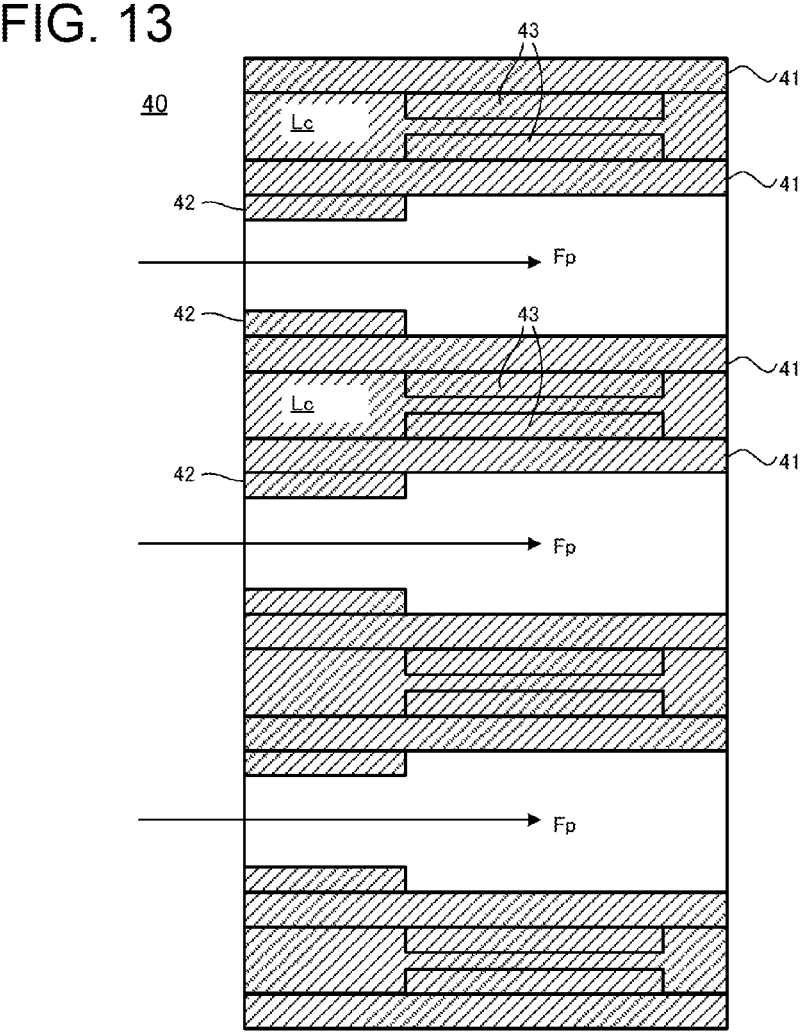
FIG. 13 is a cross-sectional view of a plasma induced flow electrode structure 40 according to a comparative example.

FIG. 13 is a cross-sectional view illustrating the plasma induced flow electrode structure 40 according to the comparative example. FIG. 14A to FIG. 14C and FIG. 15A to FIG. 15C are side views illustrating the plasma induced flow electrode structure 40 in being manufactured.

As illustrated in FIG. 13, the plasma induced flow electrode structure 40 has a stack structure made by stacking insulating plates 41, application electrode layers 42 and ground electrode layers 43 by adhesive layers Lc.

In the plasma induced flow electrode structure 40, the plurality of application electrode layers 42 exposed to the atmosphere and the plurality of ground electrode layers 43 insulated from the atmosphere are electrically independent. Therefore, the plurality of application electrodes 42 and the plurality of ground electrode 43 are required to be wired separately in parallel, and thus wiring is complicated.

Figure 14A:
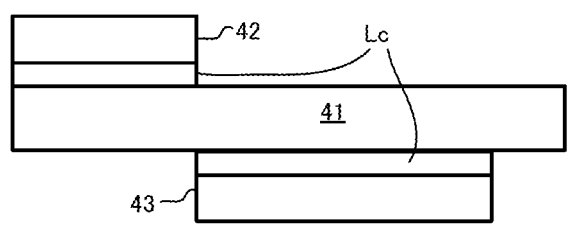
FIG. 14A to FIG. 14C and FIG. 15A to FIG. 15C are side views illustrating the plasma induced flow electrode structure 40 in being manufactured.
Figure 14B:
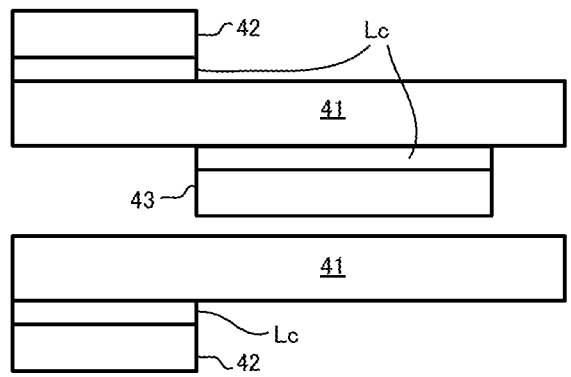
Figure 14C:
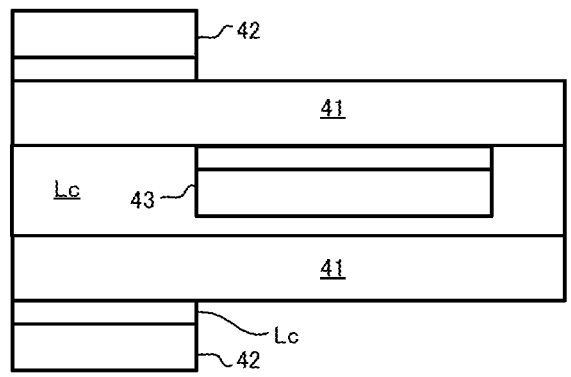

In order to fabricate the plasma induced flow electrode structure 40, for example, a next procedure can be adopted. That is, the application electrode layer 42 and the ground electrode layer 43 are bonded via the adhesive layers Lc above and below one insulating plate 41 (FIG. 14A). Then, the ground electrode layer 43 is sandwiched by another insulating plate 41 to which only the application electrode layer 42 is bonded (FIG. 14B). A space between the two insulating plates 41 is sealed with the adhesive layer Lc (or filler) (FIG. 14C).

Figure 15A:
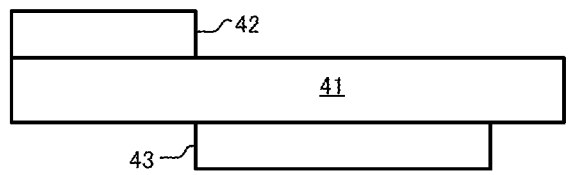
Figure 15B:
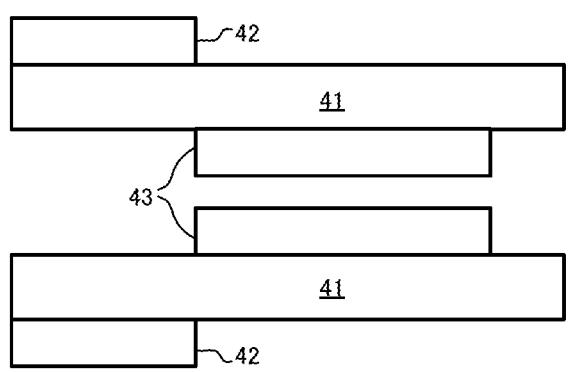
Figure 15C:
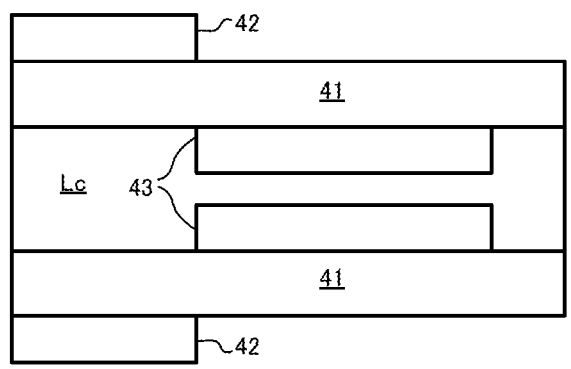

As another fabrication method, an application electrode layer 42 and a ground electrode layer 43 are directly formed above and below one insulating plate 41 by sputtering or plating (FIG. 15A). Then, the ground electrode 43 is sandwiched by another insulating plate 41 on which the application electrode 42 and the ground electrode 43 are formed (FIG. 15B). Thereafter, a space between the two insulating plates 41 is sealed with an adhesive layer Lc (or filler) (FIG. 15C).

As described above, whichever method is adopted, bonding with an adhesive or the like is necessary and a manufacturing process becomes complicated.

Further, the plasma induced flow electrode structure 40 of the stack structure is limited also in terms of a shape. In other words, for the plasma induced flow electrode structure 40 for the purpose of air purification, a shape which has parallel slits (spaces between electrodes) in parallel and in multiple stages is not necessarily optimum. For example, there is a case where a circular outer shape or concentric slits are desirable. However, for the stack structure in which the insulating plate 41, the application electrode 42 and the around electrode 43 are stacked, it is difficult to make a complicated structure.

In contrast, in the plasma induced flow electrode structure according to the embodiment, it is possible to form a plasma induced flow electrode structure which has an outer shape of a proper shape and a through hole H, comparatively easily.

Fourth Embodiment

A method of manufacturing a plasma induced flow electrode structure according to a fourth embodiment will be described. In the present embodiment, the plasma induced flow electrode structure 10 according to the first embodiment can be manufactured.

Figure 16:
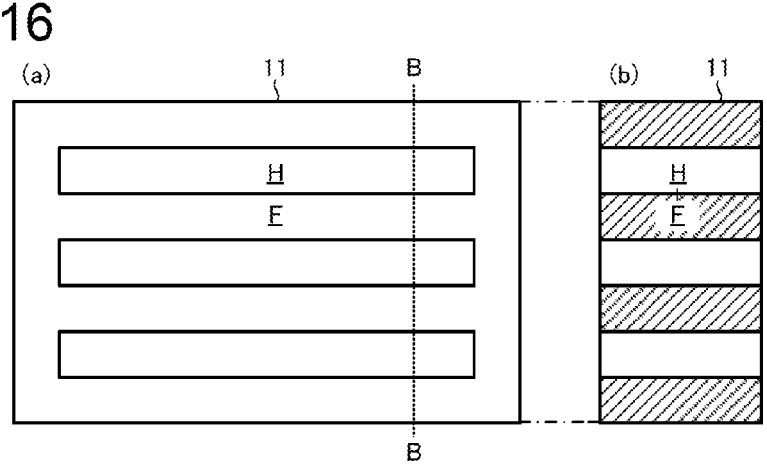
FIG. 16 to FIG. 18 are front views and cross-sectional views illustrating the plasma induced flow electrode structure 10 in being manufactured.
Figure 17:
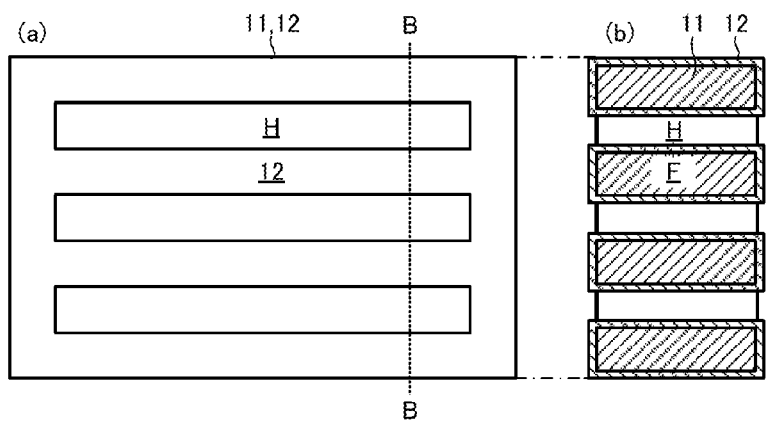
Figure 18:
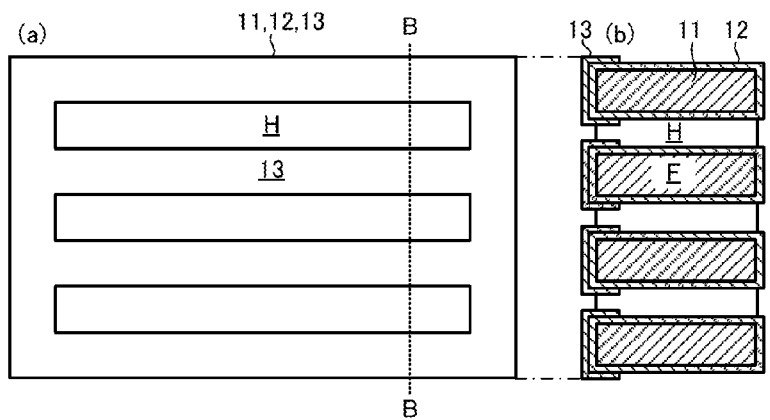

FIG. 16 to FIG. 18 are front views and cross-sectional views illustrating the plasma induced flow electrode structure 10 in being manufactured in the present embodiment. FIG. 16(h) to FIG. 18(b) are the cross-sectional views illustrating states where the plasma induced flow electrode structures 10 of FIG. 16(a) to FIG. 18(a) are cut along lines B-B, respectively.

(1) Preparation of Electrode Block 11 (Step S11, FIG. 16)

An electrode block 11 is fabricated by integral cutting from an electrode block (for example, copper block), similarly to in the third embodiment.

(2) Formation of Insulating Layer 12 (Step S12, FIG. 17)

An insulating layer 12 is formed on an electrode fin F of the electrode block 11.

In the third embodiment, since the entire surface of the electrode block 11 is not covered by the insulating layer 12, it is necessary to lay the electrode layer 13 (application electrode) at a distance from the exposed electrode fin F (ground electrode). Here, by immersion in an insulating material (resin material, for example, polyimide resin), the entire surface of the electrode block 11 is covered (formation of insulating layer 12). Consequently, limitation in position of the electrode layer 13 (application electrode) is alleviated.

In a region in which discharge is occurring, a temperature is quite high and a pin hole due to fusion or deterioration of an insulating material causes dielectric breakdown, and thus the insulating material which constitutes the insulating layer 12 is desirable to have a high heatproof temperature. As such an organic matter (resin) with a high heat resistance, there can be selected a polyimide resin, a fluorocarbon resin, a polyamide-imide resin, an allyl resin, a polyphenylene sulfide resin, a polyetherketoneketone resin, a polybenzimidazole resin, a polyetherimide resin or the like. Among the above, it is preferable to use a polyimide system resin with a high heat resistance in particular.

If durability at a fusing point is desired more, an inorganic matter may be selected as the insulating material which constitutes the insulating layer 12. For example, it is possible to adopt enamel coating or applying and baking finish of an aluminum oxide, a silicon oxide, a titanium oxide, a titanium nitride or the like. In a baking process, there is a possibility that a surface of the electrode fin F is oxidized, but it suffices that such an oxide film itself functions as an insulating coating film. Thus, oxidizing in a heat treatment is not considered, and a material of the electrode block 11 is not limited as long as the material is conductive basically, that is, aluminum, brass, copper, stainless steel or the like. Note that a resin coating film may be added after fabrication of the inorganic coating film by a baking treatment.

Figure 19A:
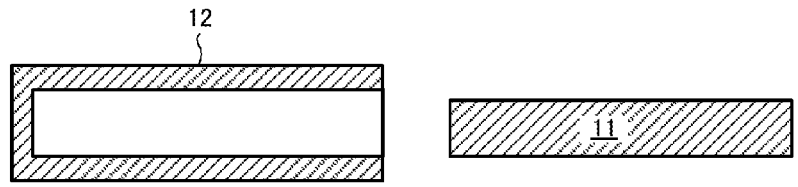
FIG. 19A and FIG. 19B are cross-sectional views illustrating the plasma induced flow electrode structure 10 in being manufactured.
Figure 19B:
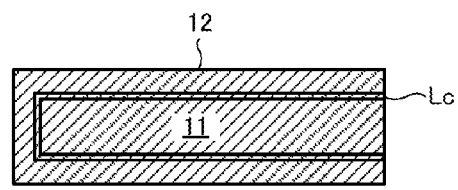

Here, if dielectric breakdown voltage on the electrode fin F is desired to be improved further, a thick insulating layer 12 (resin layer) may be formed by molding or the like, instead of fabrication of the insulating layer 12 by application. Further, it is possible to form an insulating layer 12 of an outer shell shape to wrap the electrode fin F and to make the electrode fin F embedded by an adhesive layer Lc (or filling) (see FIG. 19A, FIG. 19B). In this case, the electrode block 11 is inserted into a shell of an insulating material. As a material of the insulating layer 12 of such an outer shell shape, it is possible to adopt the organic or inorganic insulating materials described above.

(3) Formation of Electrode Layer 13 (Step S13, FIG. 18)

In the third embodiment, the electrode layer 13 is formed only in a longitudinal direction (X axis direction) of the electrode fin F. Here, the electrode layer 13 is collectively formed both on a surface S1 of the electrode block 11 and in a region inside a through hole H by about 1 min from the surface S1, by sputtering or plating. In this case, the electrode layer 13 corresponding to each through hole H is connected to each other. Thus, a conductive portion for electric connection as in the third embodiment is not necessary.

Fifth Embodiment

A method of manufacturing a plasma induced flow electrode structure according to a fifth embodiment will be described. In the present embodiment, the plasma induced flow electrode structure 10a according to the second embodiment can be manufactured.

FIG. 20 to FIG. 24 are front views and cross-sectional views illustrating the plasma induced flow electrode structure 10a in being manufactured in the present embodiment. FIG. 20(b) to FIG. 24(b) are cross-sectional views illustrating states where the plasma induced flow electrode structures 10a of FIG. 20(a) to FIG. 24(a) are cut along lines B-B, respectively.

Figure 20:
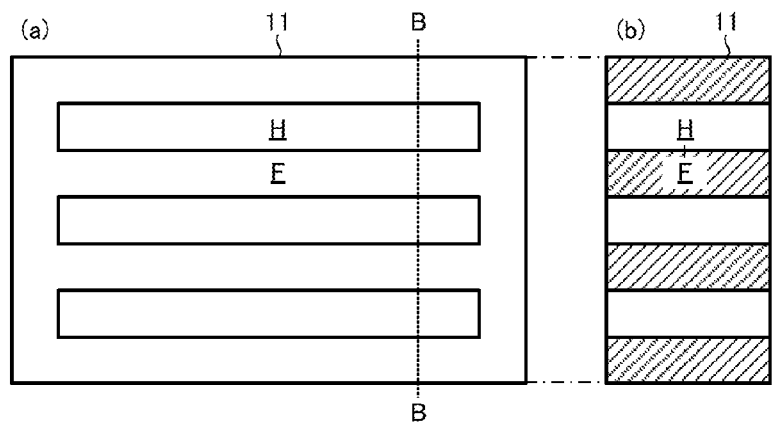
FIG. 20 to FIG. 24 are front views and cross-sectional views illustrating the plasma induced flow electrode structure 10a in being manufactured.

(1) Preparation of Electrode Block 11 (Step S11, FIG. 20)

Similarly to in the third embodiment, an electrode block 11 is fabricated by integral cutting from an electrode block (for example, copper block).

Figure 21:
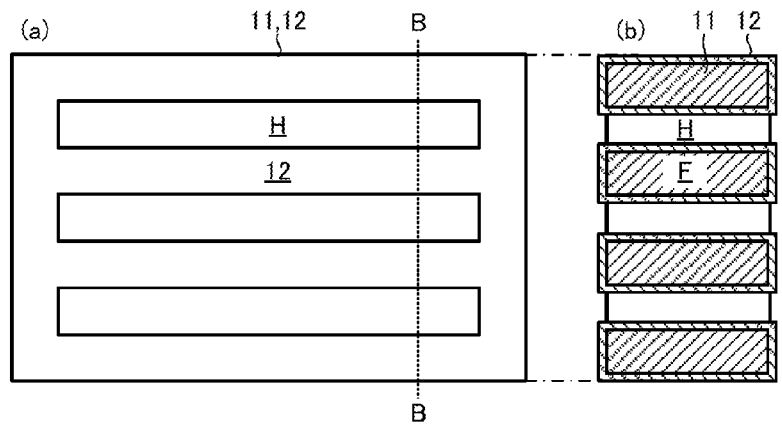
Figure 22:
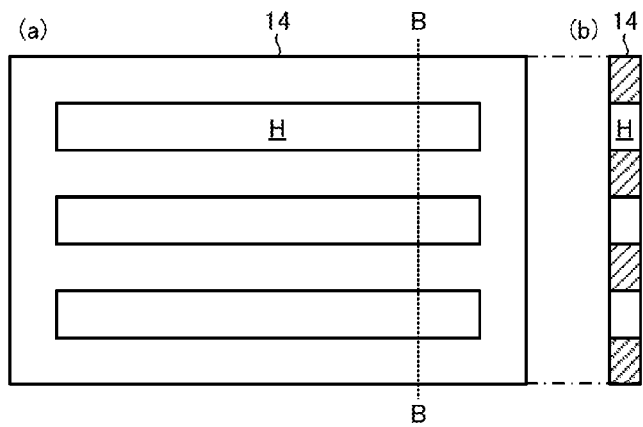

(2) Formation of Insulating Layer 12 (Step S12, FIG. 21)

An insulating layer 12 is formed on an electrode fin F of the electrode block 11. Similarly to in the fourth embodiment, the insulating layer 12 covers the entire surface of the electrode block 11, by immersion into an insulating material or baking (formation of insulating layer 12).

(3) Formation of Electrode 13 (Step S13)

Here, an electrode layer 13 is formed on an insulating member 14 in advance, and this electrode layer 13 is connected to the electrode block 11 covered by the insulating layer 12.

Figure 23:
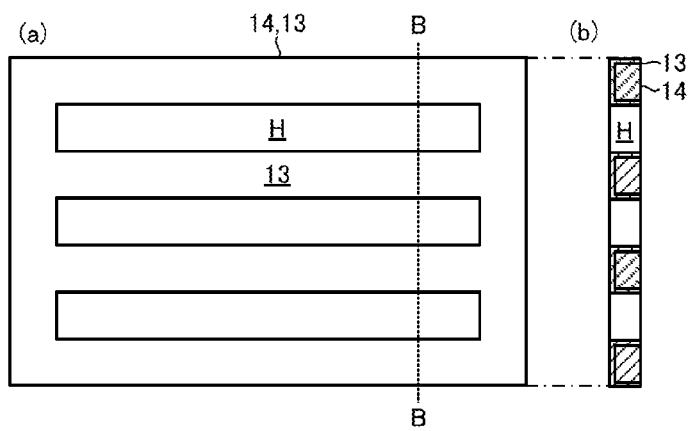

In the third and fourth embodiments, the insulating layer 12 on the electrode fin F tends to be thin. The electrode 13 is disposed on this insulating layer 12 and there is generated a place in which the electrode fin F (ground electrode) and the electrode layer 13 (application electrode) come close and their surfaces face each other. When high-frequency voltage is applied to this place, an electrostatic capacitance becomes large, leading to a bad electric efficiency. Thus, the electrode layer 13 is formed on the insulating member 14 (FIG. 22) which has almost the same cross-sectional shape as that of the electrode block 11 (FIG. 23).

The insulating member 14 is made of an insulator (dielectric) such as a resin and a ceramic, and has for example a fin shape of about 3 mm in thickness. On the insulating member 14, the electrode layer 13 (conductive portion (application electrode)) is formed in the entire surface except an adhesive surface to the electrode block 11, by sputtering, plating or the like (see FIG. 23). The insulating member 14 where the electrode layer 13 is formed is referred to as an application fin Fa.

Note that the electrode layer 13 can be formed by formation (plating, sputtering or the like) of a conductive layer in a state where the adhesive surface of the insulating member 14 is masked. Further, an electrode layer 13 may be formed as a result of forming a conductive layer on the entire surface of the insulating member 14 and thereafter peeling the conductive layer of only the adhesive surface.

Figure 24:
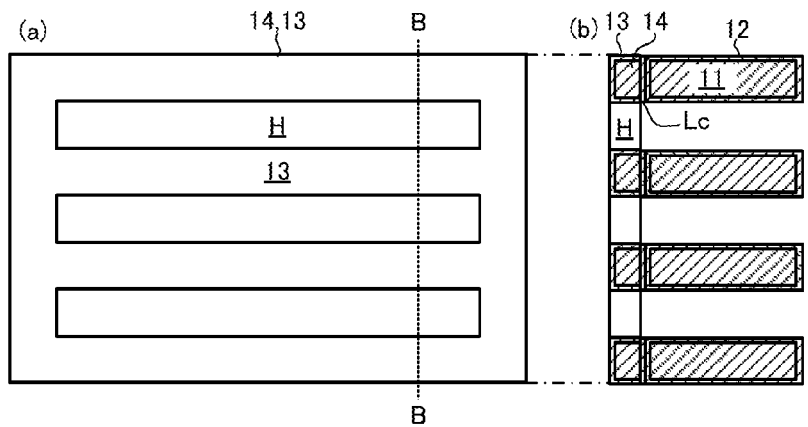

The electrode block 11 covered by the insulating layer 12 and the insulating member 14 where the electrode layer 13 is formed can be connected by being bonded with an adhesive or the like (see FIG. 24).

MODIFICATION EXAMPLE

In the fifth embodiment, a corner portion of a cross section of the electrode fin F is close to the electrode layer 13. In this case, generation of a plasma induced flow is carried out without hindrance, but an electric field on an electrode fin F (ground electrode) side becomes large in a corner portion with a small curvature radius and a discharge region is also concentrated. Therefore, there is a possibility that deterioration of the relevant surrounding insulating layer 12 is accelerated. Further, in a case where an adhesive is used for adhesion of the electrode fin F and the application fin Fa, there is a possibility that the adhesive squeezed out from a contact surface covers an end surface of the application electrode, thereby to hamper generation of the plasma induced flow.

Figure 25A:
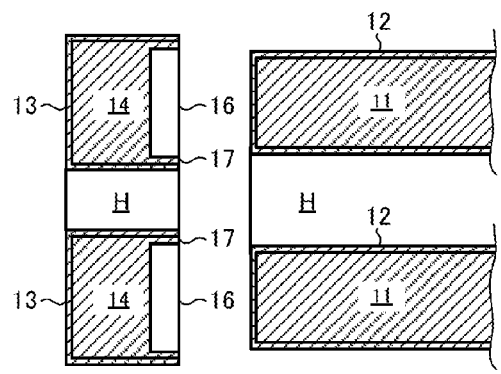
FIG. 25A, FIG. 25B, FIG. 26A, and FIG. 26B are cross-sectional views illustrating the plasma induced flow electrode structure 10a in being manufactured.
Figure 25B:
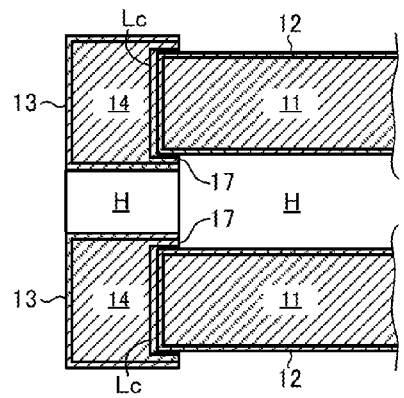

Thus, it is considered to provide a recessed portion 16 in the insulating member 14 to cover the corner of the electrode fin F (see FIG. 25A to 25C). The recessed portion 16 may have a shape (FIG. 25A, FIG. 25B) to correspond to an end portion of the electrode fin F, for example an almost rectangular parallelepiped shape, and, for example, its depth may be about 1 mm. As described above, as a result that the end surface of the electrode fin F gets into the recessed portion 16 of the insulating member 14, concentration or the like of the electric field in the corner of the electrode fin F can be avoided. Further, this recessed portion 16 also functions as a guide to prevent displacement in adhesion (adhesive layer Lc) of the electrode fin F and the insulating material 14 (FIG. 25B).

A projecting portion 17 is disposed in a periphery of the recessed portion 16. This projecting portion 17 is disposed in a periphery of a through hole H of the insulating member 14 and is engaged with a through hole H of the electrode block 11.

In this configuration, when a side wall of the recessed portion 16 is thin, the electrode layer 13 (application electrode) and the electrode fin F (ground electrode) come close, and there is a possibility that an electrostatic capacitance becomes large. Therefore, it is preferable to make the side wall of the recessed portion 16 thick to some extent.

Figure 26A:
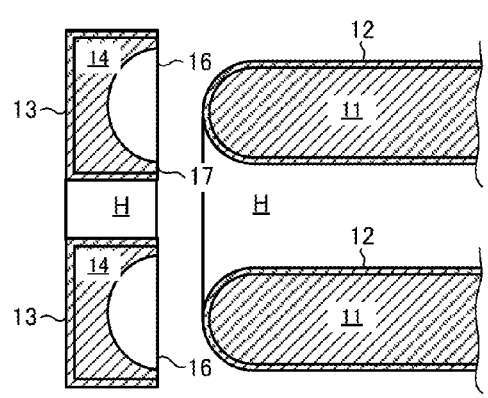
Figure 26B:
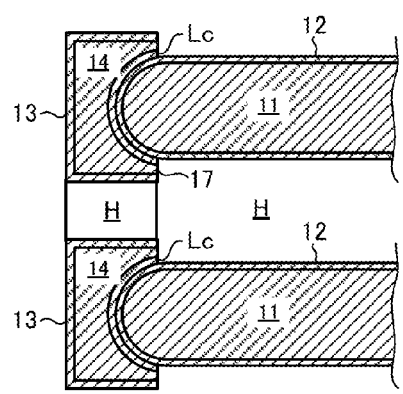

In order to avoid increase of the electrostatic capacity, an end portion (surface S1) of an electrode fin F and a recessed portion 16 of an insulating member 14 may have rounded shapes (curved surface shapes, for example, hemispheric shape) (see FIG. 26A, FIG. 26B). In this case, the recessed portion 16 of the insulating member 14 is engaged with a curved surface shape of the end portion of the electrode fin F via an adhesive layer Lc (see FIG. 26B). By configuring as above, a place where a curvature radius is extremely small does not exist, so that concentration or the like of an electric field in the corner of the electrode fin F can be avoided more effectively.

Hereinafter, examples related to the method of manufacturing the plasma induced flow electrode structure will be described.

First Example

In a first example, the plasma induced flow electrode structure 10 is fabricated by the manufacturing method according to the third embodiment (see FIG. 1A, FIG. 1B, FIG. 9 to FIG. 12).

When sinusoidal voltage of 10 kHz in frequency and 7 kV is applied between the electrode 13 (application electrode) and the electrode block 11 (ground electrode), discharge is verified. Further, it is also verified that a plasma induced flow is generated, by a streamer provided on a downstream side of the electrode block 11. According to a tester, an electrostatic capacitance of the plasma induced flow electrode structure 10 is about 100 pF.

Second Example

In a second example, the plasma induced flow electrode structure 10a is fabricated by the manufacturing method according to the fifth embodiment (see FIG. 2A, FIG. 2B, FIG. 20 to FIG. 24)

Concretely, the plasma induced flow electrode structure is fabricated by bonding the ground electrode fin (combination of electrode block 11 and insulating layer 12 of FIG. 10) according to the first example and the application fin Fa (combination of insulating member 14 and electrode layer 13 of FIG. 23).

In this configuration, when voltage is applied under the same condition as in the first example, discharge and an induced flow are verified similarly to in the first example.

Moreover, an electrostatic capacitance is curtailed to one-sixth the electrostatic capacitance of the first example, and an effect of the third embodiment can be verified.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A plasma induced flow electrode structure comprising:
   an electrode block including a first and a second surface and a plurality of through holes penetrating between the first and second surfaces;
   an insulating layer disposed on the first surface and inside the through holes; and
   an electrode layer disposed on the insulating layer on the first surface.

2. The plasma induced flow electrode structure of claim 1, wherein the electrode layer extends onto the insulating layer inside the through holes.

3. The plasma induced flow electrode structure of claim 1, wherein the electrode layer is not disposed in a part of first areas on the first surface and around the through holes.

4. The plasma induced flow electrode structure of claim 3, further comprising
   a second electrode layer disposed in a part of second areas on the second surface and around the through holes.

5. The plasma induced flow electrode structure of claim 1, further comprising
   an insulating plate disposed between the insulating layer and the electrode layer, the insulating plate including third and fourth surfaces and a plurality of second through holes, the second through holes penetrating between the third and fourth surfaces and corresponding to the through holes.

6. The plasma induced flow electrode structure of claim 5, wherein the electrode layer extends to inside the second through holes.

7. The plasma induced flow electrode structure of claim 5, wherein the insulating plate includes projecting portions disposed around the second through holes and engaged with the through holes.

8. The plasma induced flow electrode structure of claim 5, wherein the first surface of the electrode block includes a plurality of roundish shapes between the through holes; and
   wherein the insulating plate includes a plurality of roundish recesses engaged with the roundish shapes.

9. The plasma induced flow electrode structure of claim 1, wherein sizes of the through holes vary in correspondence with distances from a center of the electrode block.

10. The plasma induced flow electrode structure of claim 1,
    wherein the insulating layer includes a polyimide system resin.

11. A plasma induced flow generation device, comprising:
    the plasma induced flow electrode structure of claim 1; and
    a power supply that apply AC voltage to between the electrode layer and the electrode block.

12. A method of manufacturing a plasma induced flow electrode structure, the method comprising:
    preparing an electrode block including a first and a second surface and a plurality of through holes penetrating between the first and second surfaces;
    forming an insulating layer on the first surface and inside the through holes; and
    forming an electrode layer on the insulating layer of the first surface.

13. The method of manufacturing the plasma induced flow electrode structure of claim 12,
    wherein the step of forming the insulating layer includes bonding an insulating film to the electrode block.

14. The method of manufacturing the plasma induced flow electrode structure of claim 12,
    wherein the step of forming the insulating layer includes inserting the electrode block into a shell of an insulating material.

15. The method of manufacturing the plasma induced flow electrode structure of claim 12, further comprising
    preparing an insulating plate including a third and a fourth surface, a plurality of second through holes, and the electrode layer, the second through holes penetrating between the third and fourth surfaces and corresponding to the through holes, the electrode layer being disposed on the third surface,
    wherein the step of forming the electrode layer includes bonding the fourth surface of the insulating plate to the insulating layer on the first surface.

* * * * *